(12) United States Patent
Bledsoe et al.

(10) Patent No.: US 9,132,026 B2
(45) Date of Patent: Sep. 15, 2015

(54) ADJUSTABLE PAD AND ORTHOPEDIC KNEE BRACE INCLUDING SAME

(75) Inventors: Gary R. Bledsoe, Mansfield, TX (US); James Leo Dillion, Northlake, TX (US)

(73) Assignee: Breg, Inc., Carlsbad, CA (US)

( * ) Notice: Subject to any disclaimer, the term of this patent is extended or adjusted under 35 U.S.C. 154(b) by 0 days.

(21) Appl. No.: 13/307,869

(22) Filed: Nov. 30, 2011

(65) Prior Publication Data
US 2012/0143111 A1 Jun. 7, 2012

Related U.S. Application Data

(60) Provisional application No. 61/418,711, filed on Dec. 1, 2010.

(51) Int. Cl.
*A61F 5/00* (2006.01)
*A61F 5/01* (2006.01)

(52) U.S. Cl.
CPC ....... *A61F 5/0123* (2013.01); *A61F 2005/0174* (2013.01)

(58) Field of Classification Search
CPC ..... A61F 5/0123; A61F 5/0125; A61F 5/013; A61F 2005/0132
USPC ................... 602/26, 20, 16, 27, 23
See application file for complete search history.

(56) References Cited

U.S. PATENT DOCUMENTS

| 4,817,588 A * | 4/1989 | Bledsoe .................... 602/16 |
| 6,413,232 B1 | 7/2002 | Townsend et al. |
| 2003/0153856 A1 | 8/2003 | Seligman et al. |

OTHER PUBLICATIONS

International Preliminary Report on Patentability issued Mar. 11, 2013, for related Intl. Appln. No. PCT/US2011/062658.
International Search Report issued Jun. 29, 2012, corresponding to Intl. Appln. No. PCT/US2011/062658.

* cited by examiner

*Primary Examiner* — Victoria J Hicks
(74) *Attorney, Agent, or Firm* — K&L Gates LLP

(57) ABSTRACT

An orthopedic apparatus includes an orthopedic knee brace including at least one hinge, an adjustable pad removably attachable to the hinge, the adjustable pad including a top plate, a base plate, an adjuster located between the top plate and the base plate, at least one ramp including a plurality of ramp angles, the ramp inclined so that at least two of the ramp angles are spaced differently from a foot of the ramp, and at least one spoke positioned and arranged to selectively engage one of the ramp angles of the at least one ramp to set an overall height of the pad, and wherein the adjustable pad is installable on the brace hinge for adjusting the side force applied to the user's knee to help relieve the pain of medial or lateral unicompartmental osteoarthritis while providing additional stability for ligament or cartilage insufficiencies.

18 Claims, 11 Drawing Sheets

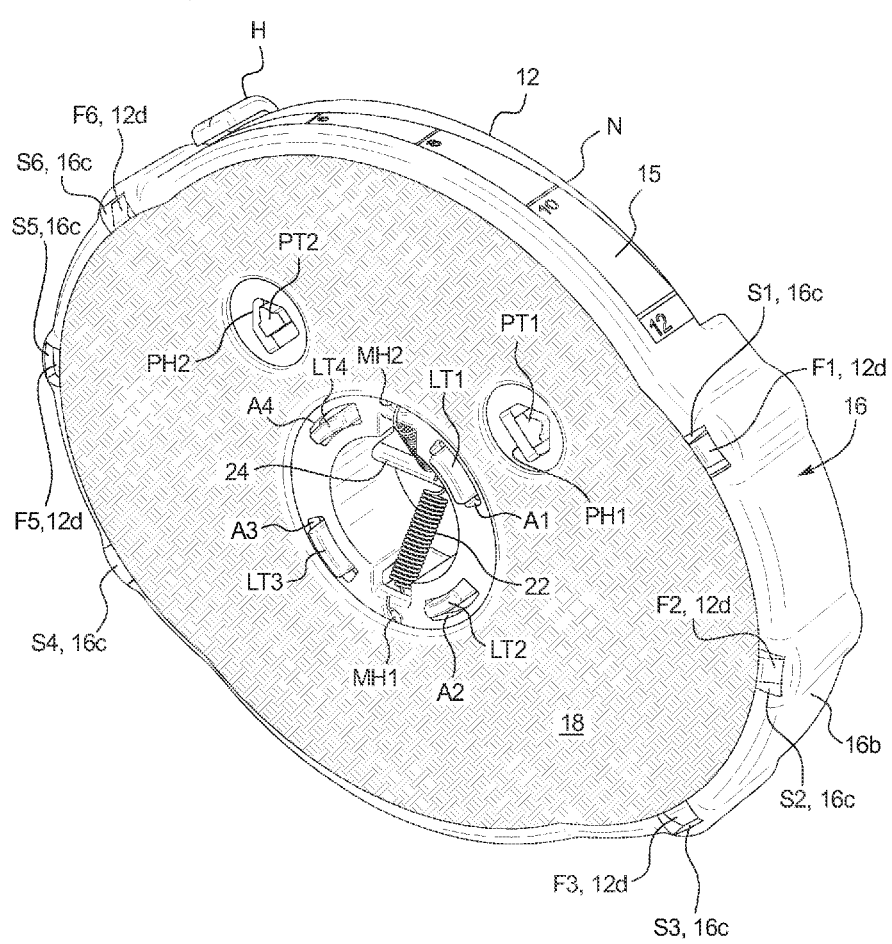

ADJUSTABLE PAD AND ORTHOPEDIC KNEE BRACE INCLUDING SAME

PRIORITY CLAIM

This application claims priority to and the benefit of U.S. Provisional Patent Application No. 61/418,711, entitled, "ADJUSTABLE PAD FOR AN ORTHOPEDIC KNEE BRACE", filed Dec. 1, 2010, the entire contents of which are incorporated herein by reference and relied upon.

BACKGROUND

The present disclosure relates generally to orthopedics and more particularly to dynamic knee bracing.

Unicompartmental osteoarthritis of the knee affects millions of individuals. Most nonsurgical management of this progressive disease is primarily directed at reducing inflammation and pain with medication. Evidence supports the clinical efficacy of bracing for managing osteoarthritis of the knee. In some patients, bracing significantly reduces pain, increases function, and reduces excessive loading to the damaged compartment. A variety of health and functional status instruments, techniques and investigations, have been used to evaluate the unloading capabilities of such braces. The braces have been shown to load share and thus reduce the stresses in the degenerated medial compartment of the knee.

A need exists for an improved device for treating and/or aiding unicompartmental osteoarthritis.

SUMMARY

The adjustable pad in general is a pad that is placed between the inside or outside of the user's knee and the brace, and which is turned to produce a corresponding translational expansion or contraction of the pad to respectively increase or decrease pressure applied to the user's knee. The adjustable pad can be installed on a double upright hinged functional knee brace forming an overall orthopedic apparatus. The adjustable pad and knee brace provide an apparatus and method of adjusting the side force applied to the user's knee to help relieve the pain of medial or lateral unicompartmental osteoarthritis while providing additional stability for ligament or cartilage insufficiencies.

To the above ends, and without limiting the following description, in a first aspect of the present disclosure, an orthopedic apparatus includes: an orthopedic knee brace including at least one hinge; and an adjustable pad removably attachable to the orthopedic knee brace, the adjustable pad including a top plate, a base plate, an adjuster located between the top plate and the base plate, at least one ramp including a plurality of ramp angles, the ramp inclined so that at least two of the ramp angles are spaced differently from a foot of the ramp, at least one spoke positioned and arranged to selectively engage one of the ramp angles of the at least one ramp, and wherein (i) the at least one ramp is provided on one side of the adjuster and the at least one spoke is provided on one of the top plate or the base plate, (ii) at least one ramp is provided on each of two sides of the adjuster and at least one spoke is provided on both the top and base plates, (iii) the at least one ramp is provided on one of the top or the base plate and the at least one spoke is provided on a mating side of the adjuster, or (iv) at least one ramp is provided on both the top and the base plate and at least one spoke is provided on each of two sides of the adjuster.

In accordance with a second aspect of the present disclosure, which may be used in combination with the first aspect, the adjustable pad is removably attachable to the orthopedic knee brace via a hook and loop attachment.

In accordance with a third aspect of the present disclosure, which may be used in combination with any one or more of the preceding aspects, the knee brace includes medial and lateral hinges, and wherein the adjustable pad can be selectively attached to either of the hinges.

In accordance with a fourth aspect of the present disclosure, which may be used in combination with any one or more of the preceding aspects, for at least (iv) the top plate and the base plate are positioned relative to each other such that the circular ramp of the top plate is concentric with and adjacent to the circular ramp of the base plate.

In accordance with a fifth aspect of the present disclosure, which may be used in combination with any one or more of the preceding aspects, for at least (iii) or (iv) the spoke includes at least one of an upper ramp angle that is shaped to mate with the ramp angles of the top plate and a lower ramp angle that is shaped to mate with the ramp angles of the base plate.

In accordance with a sixth aspect of the present disclosure, which may be used in combination with any one or more of the preceding aspects, for at least (iii) or (iv) at least one of the top plate and the base plate includes N number of ramps, and the adjuster ring includes N number of spokes for operation with the N number of top and/or base plate ramps.

In accordance with a seventh aspect of the present disclosure, which may be used in combination with any one or more of the preceding aspects, the adjuster rotates relative to the top and base plates.

In accordance with an eighth aspect of the present disclosure, which may be used in combination with any one or more of the preceding aspects, one of the top or the base plates includes at least one tab that extends in a cantilevered manner from a wall of the plate, the adjuster including at least one feature for receiving a mating feature of the at least one tab, the receiving of the feature and the mating feature coinciding with an adjustment setting of the adjustable pad.

In accordance with a ninth aspect of the present disclosure, which may be used in combination with the eighth aspect, the adjuster includes an interior ring forming the at least one feature, and wherein the at least one spoke can be secured between the inner ring and an outer ring of the adjuster.

In accordance with a tenth aspect of the present disclosure, which may be used in combination with the eighth aspect, the other of the top or base plate defines at least one aperture for receiving the at least one tab to allow the adjustable pad to be compressed without the at least one tab abutting the other of the top or base plate.

In accordance with an eleventh aspect of the present disclosure, which may be used in combination with any one or more of the preceding aspects, the adjuster includes a handle for a user to rotate the adjuster for setting adjustment, the handle extending from the adjuster an as to reside outside of the top plate and base plate when the plates are mated.

In accordance with a twelfth aspect of the present disclosure, which may be used in combination with any one or more of the preceding aspects, one of the base plate or top plate includes at least one (e.g., spring-like) finger extending from a wall of the plate, and the other of the base plate or the top plate includes at least one receiver post or aperture for capturing the at least one finger for stabilizing the base and top plates when the plates are moved towards or away from each other.

In accordance with a thirteenth aspect of the present disclosure, which may be used in combination with any one or more of the preceding aspects, the at least one ramp is compressed against the at least one spoke by at least one spring.

In accordance with a fourteenth aspect of the present disclosure, which may be used in combination with the thirteenth aspect, the at least one spring is (i) an extension spring in mechanical communication with the top and base plates or (ii) a compression spring applying a compression force to the top plate or the base plate.

In accordance with a fifteenth aspect of the present disclosure, which may be used in combination with any one or more of the preceding aspects, one of the top or the base plate is configured to be removably attached to the knee brace, while the other of the top or the base plate includes or is attached to padding for comfortable engagement with a user of the orthopedic apparatus.

In accordance with a sixteenth aspect of the present disclosure, which may be used in combination with any one or more of the preceding aspects, one of the top plate or the base plate includes a lip that extends past the other of the top or base plate, the lip sized and arranged to fit around the periphery of the at least one hinge to provide mounting stability.

In accordance with a seventeenth aspect of the present disclosure, which may be used in combination with any one or more of the preceding aspects, for at least (i) or (ii), at least one ramp on the adjuster engages at least one spoke provided on the base plate, and wherein a fastener extends through the base plate and is attached to the top plate.

In accordance with an eighteenth aspect of the present disclosure, which may be used in combination with any one or more of the preceding aspects, an orthopedic apparatus includes: an orthopedic knee brace including at least one hinge; and an adjustable pad removably attachable to the orthopedic knee brace, the adjustable pad including a plate including at least one semi-cylindrical ramp having a plurality of ramp angles, at least two of the ramp angles spaced differently from a primary wall of the plate, an adjuster located adjacent to the plate and including at least one spoke shaped and positioned to selectively engage the ramp angles of the at least one ramp to set a desired overall height of the adjustable pad, and at least one spring is positioned and arranged to compress the plate to the adjuster regardless of which ramp angle that the at least one spoke is engaged.

In accordance with a nineteenth aspect of the present disclosure, which may be used with any one or more of the preceding aspects in combination with the eighteenth aspect, the plate is a first plate and the at least one semi-cylindrical ramp is a first semi-cylindrical ramp, and which includes a second plate including at least one second semi-cylindrical ramp having a plurality of ramp angles at least two of which are spaced differently from a primary wall of the second plate, the at least one spoke selectively engaging one of the ramp angles of the at least one second semi-cylindrical ramp of the second plate, the at least one spring positioned and arranged to compress the first and second plates and the adjuster regardless of the position of the at least one spoke.

In accordance with a twentieth aspect of the present disclosure, which may be used with any one or more of the preceding aspects in combination with the eighteenth aspect, the ramp angles of the at least one semi-cylindrical ramp increase sequentially in distance from the primary wall from a most-compressed adjuster pad ramp angle to a most-expanded adjuster pad ramp angle.

In accordance with a twenty-first aspect of the present disclosure, which may be used in combination with any one or more of the preceding aspects, an orthopedic apparatus includes: an orthopedic knee brace including at least one hinge; and an adjustable pad removably attachable to the orthopedic knee brace, the adjustable pad including an adjuster including at least one semi-cylindrical ramp having a plurality of ramp angles, at least two of the ramp angles spaced differently from a foot of the ramp, a plate located adjacent to the adjuster and including at least one spoke positioned to be selectively engaged by the ramp angles of the at least one ramp to set a desired overall height of the adjustable pad, and at least one spring positioned and arranged to compress the adjuster to the plate regardless of which ramp angle has been engaged to the at least one spoke.

In accordance with a twenty-second aspect of the present disclosure, which may be used with any one or more of the preceding aspects in combination with the twenty-first aspect, the plate is a first plate and the at least one spoke is a first spoke, and which includes a second plate including at least one second spoke, and wherein the at least one semi-cylindrical ramp is a first at least one semi-cylindrical ramp and the adjuster includes a second at least one semi-cylindrical ramp engaging the second spoke, the at least one spring positioned and arranged to compress the first and second plates and the adjuster together regardless of the position of the adjuster.

In accordance with a twenty-third aspect of the present disclosure, which may be used with any one or more of the preceding aspects in combination with the twenty-first aspect, the ramp angles of the at least one semi-cylindrical ramp increase sequentially in distance from the foot of the ramp from a most-compressed adjuster pad ramp angle to a most-expanded adjuster pad ramp angle.

In accordance with a twenty-fourth aspect of the present disclosure, which may be used in combination with any one or more of the preceding aspects, an orthopedic bracing method includes: enabling an orthopedic knee brace to place a user-selectable side load on a user's knee by allowing the user to manipulate an adjuster, wedging the adjuster at different locations within first and second plates located on either side of the adjuster, thereby sequentially increasing a distance between the adjuster and at least one opposing wall of the respective first and second plates to sequentially increase the side load; and compressing the first and second plates to the adjuster throughout the sequential increasing.

In accordance with a twenty-fifth aspect of the present disclosure, which may be used with any one or more of the preceding aspects in combination with the twenty-fourth aspect, wedging the adjuster includes moving an inclined ramp against a fixed spoke.

In accordance with a twenty-sixth aspect of the present disclosure, which may be used with any one or more of the preceding aspects in combination with the twenty-fourth aspect, wedging the adjuster includes moving a spoke against a fixed inclined ramp.

In accordance with a twenty-seventh aspect of the present disclosure, which may be used with any one or more of the preceding aspects in combination with the twenty-fourth aspect, the method includes enabling manipulation of the adjuster (i) in a first direction to sequentially increase the distance and the side load and (ii) in a second direction to sequentially decrease the distance and the side load.

In accordance with a twenty-eighth aspect of the present disclosure, which may be used with any one or more of the preceding aspects in combination with the twenty-seventh aspect, the method includes compressing the first and second plates throughout the sequential decreasing.

In accordance with a twenty-ninth aspect of the present disclosure, any of the structure and functionality illustrated and described in connection with FIGS. 1 to 11 may be used in combination with any of the structure and functionality illustrated and described in connection with any of the other of FIGS. 1 to 11 and with any one or more of the preceding aspects.

In light of the above aspects, it should be appreciated that it is an advantage of the present invention to provide an improved orthopedic knee brace.

It is another advantage of the present invention to provide an improved telescoping compressible and expandable pad for an orthopedic knee brace.

It is a further advantage of the present disclosure to provide an adjustable orthopedic knee brace pad that is lightweight but sturdy.

It is yet another advantage of the present disclosure to provide an adjustable orthopedic knee brace pad that can be placed on either side of the user's knee.

It is yet a further advantage of the present disclosure to provide an adjustable orthopedic knee brace pad that provides an even load around a periphery of the pad.

It is still another advantage of the present disclosure to provide an adjustable orthopedic knee brace pad that is stable when placed on the knee brace but is readily removeable from the knee brace.

Additional features and advantages are described herein, and will be apparent from the following Detailed Description and the figures.

BRIEF DESCRIPTION OF THE FIGURES

FIG. 5B is a perspective view of one embodiment of an assembled adjustable pad of the present disclosure shown from the top plate side of the pad.

DETAILED DESCRIPTION

First Primary Embodiment

Figure 1:
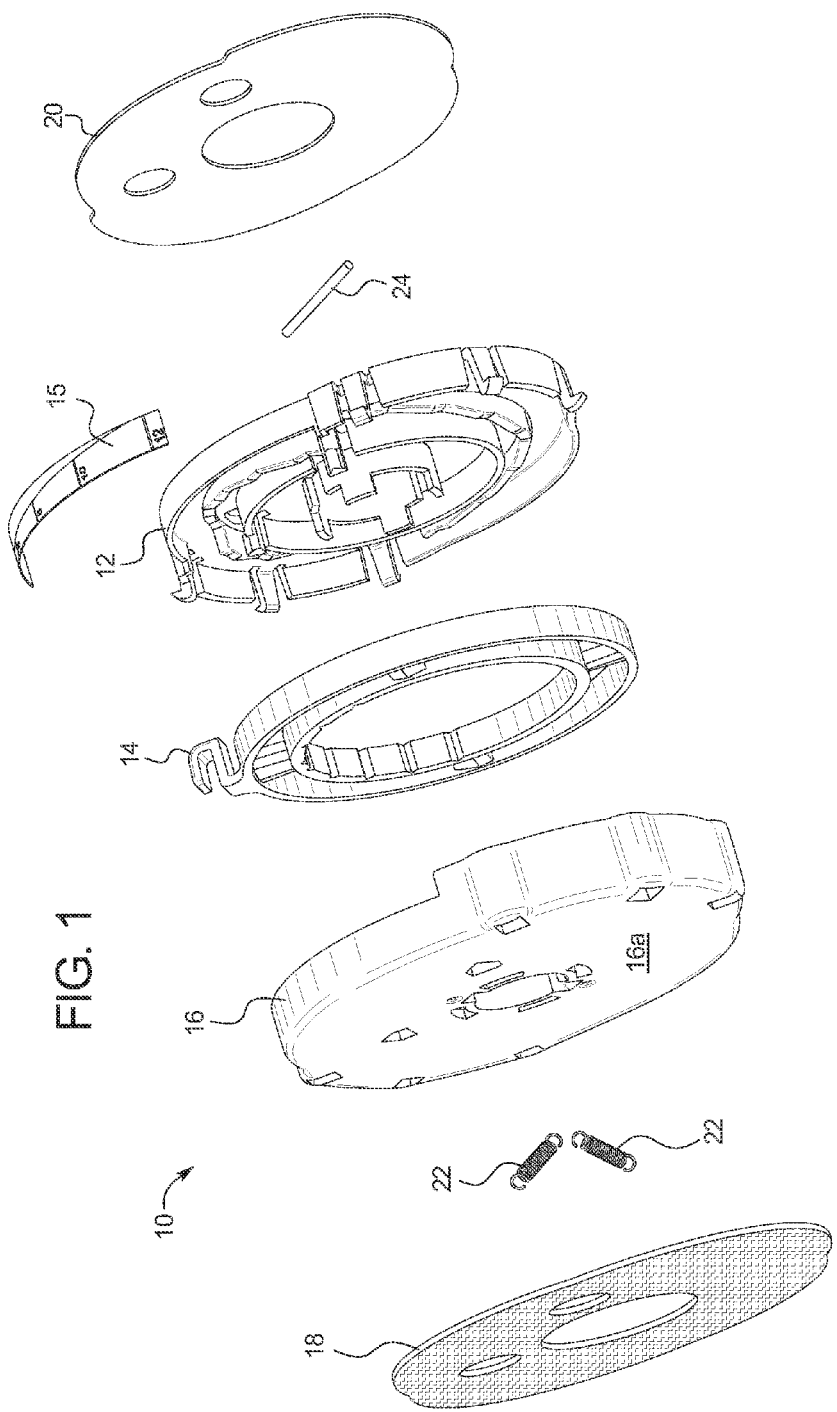
FIG. 1 is an exploded perspective view of one primary embodiment of an adjustable pad of the present disclosure including, from left to right, a hook or pile sheet, springs, a top plate, an adjuster ring, a base plate, a rod and a base pile or hook layer.

One primary embodiment for an adjustable pad is shown and described in connection with adjustable pad 10 and FIGS. 1 to 7 as follows. FIG. 1 is an exploded view showing the different pieces of adjustable pad 10. From left to right, hook sheet 18 is adhered to the top wall 16a of top plate 16. The hook sheet 18 indexes a hook surface that removably attaches to a pile surface of a cushioned or gel encapsulating pad 19 illustrated below that has inner cushioning foam or gel. The outer surface of the cushion is soft, e.g., felt, and abuts the user's knee. The inner surface of the cushion includes pile material that attaches to hook material provided on the outer surface of sheet 18. Hook sheet 18 is adhered to an assembly that includes top plate 16, an adjuster ring 14 and a base plate 12, discussed in detail below. Top plate 16, adjuster ring 14 and base plate 12 can each be made of plastic, metal or some combination thereof. A base pile layer 20 is adhered to the inside surface of base plate 12. Base pile layer 20 enables the assembled adjustable pad 10 to be removably connected to hook material provided on either hinge of a knee brace (FIG. 7). A label 15 is provided on, e.g., adhered to, base plate 12 to provide an indication of the current state of expansion for adjustable pad 10.

For purposes of disclosure, sheet 18 has been described as having hook material, while layer 20 has been described as having pile material. It should be appreciated that for any embodiment of the adjustable pads of the present disclosure, a surface can have hook or pile material interchangeably.

Figure 2:
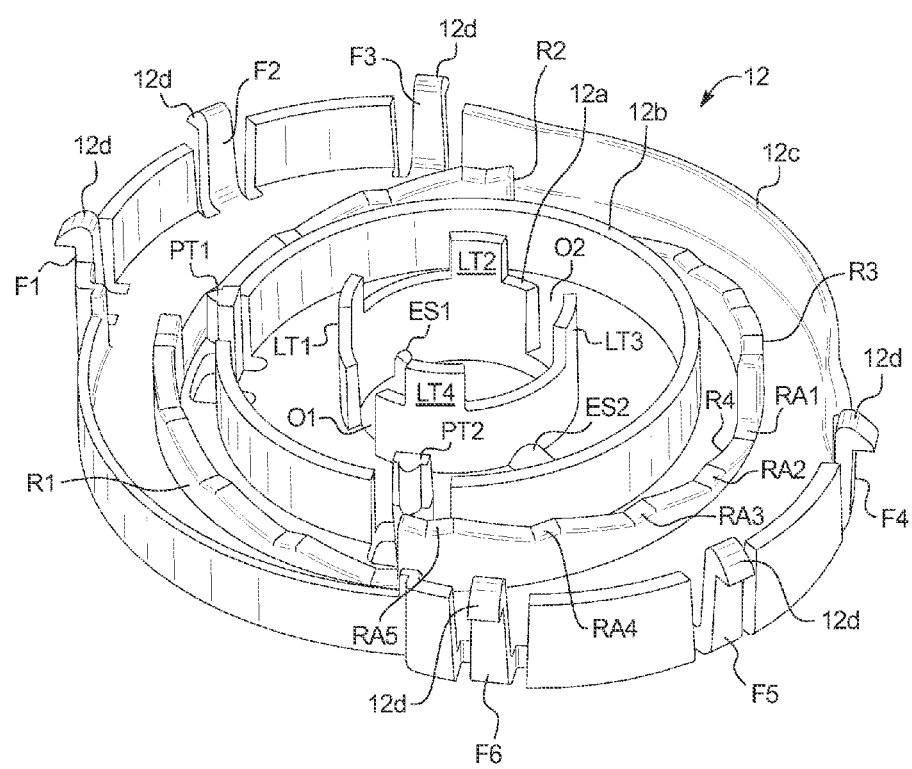
FIG. 2 is a perspective view of one embodiment of a base plate of the adjustable pad of the present disclosure.
Figure 3:
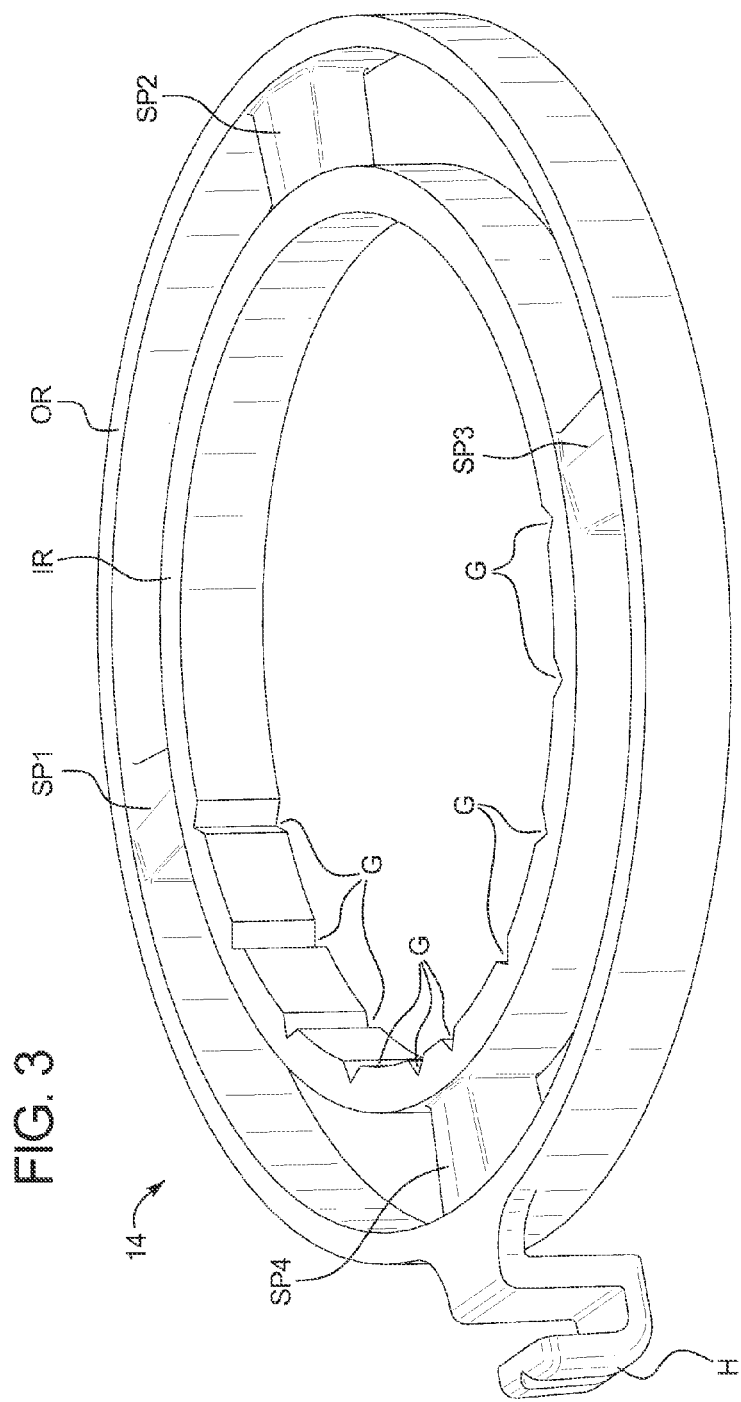
FIG. 3 is a perspective view of one embodiment an adjuster ring of the adjustable pad of the present disclosure.

FIG. 2. illustrates base plate 12 in more detail, while FIG. 3 illustrates adjuster ring 14 in more detail. In FIG. 2, a second ring 12b residing outwardly from a center ring 12a of base plate 12 is interrupted by two spring-like, cantilevered polygonal tabs PT1 and PT2, spaced about 90° apart from each other at approximately nine o'clock and six o'clock, respectively, in FIG. 2. Cantilevered polygonal tabs PT1 and PT2 each have a V-shaped projection protruding radially outwardly from an inner rectangular portion of the tabs. The V-shaped projections are indexer tabs that operate as spring fingers to snap into and out of mating female V-shaped grooves G located on the inner surface of the innermost ring IR of adjuster ring 14 (FIG. 3). The operation and purpose of the V-shaped projections and grooves G are discussed in more detail below.

Base plate 12 of FIG. 2 also illustrates an inner ring 12a has four longitudinally extending semi-cylindrical tabs LT1 to LT4. Longitudinally extending tabs LT1 to LT4 of base plate 12 extend through semi-cylindrical apertures A1 to A4, respectively, formed in top plate 16 shown in FIG. 4 (only three apertures A1, A2 and A4 are visible in FIG. 4). Likewise, polygonal tabs PT1 and PT2 of base plate 12 extend into polygonal, five-sided holes PH1 and PH2, respectively, formed in the top plate 16.

When adjustable pad 10 is fully contracted, such that base plate 12 sits as deep as possible into top plate, semi-cylindrical or arched apertures A1 to A4 allow the like-shaped longitudinally extending tabs LT1 to LT4 to extend respectively through apertures A1 to A4 and outwardly past the predominantly solid outer surface 16a of top plate 16. Likewise, polygonal tabs PT1 and PT2 are allowed to extend through polygonal holes PH1 and PH2 and outwardly past the predominantly solid outer surface 16a of top plate 16. Polygonal holes PH1 and PH2 are oversized as needed to allow polygonal tabs PT1 and PT2 to flex radially back and forth within polygonal holes PH1 and PH2. The distal portions of each of the tabs LT1 to LT4, PT1 and PT2 extending past the solid outer surface 16a of top plate 16 are covered by the felt cushion attached to hook sheet 18 and thus are not felt or sensed by the patient.

On the other hand, when adjustable pad 10 is fully telescoped and expanded, longitudinally extending tabs LT1 to LT4 of base plate 12 even though removed from apertures A1 to A4 of top plate 16 are still able to maintain sliding contact with the outer surfaces of centrally located semi-cylindrical tabs CT1 and CT2 extending longitudinally inwardly within top plate 16. The sliding contact between the inside surfaces of longitudinally extending tabs LT1 to LT4 of base plate 12 and the outer surfaces of semi-cylindrical tabs CT1 and CT2 of top plate 16 throughout the entire range of motion for adjustable pad 10 is accordingly achieved, provides stability and protects against top plate 16 and base plate 12 tilting against each other during adjustment.

Figure 4:
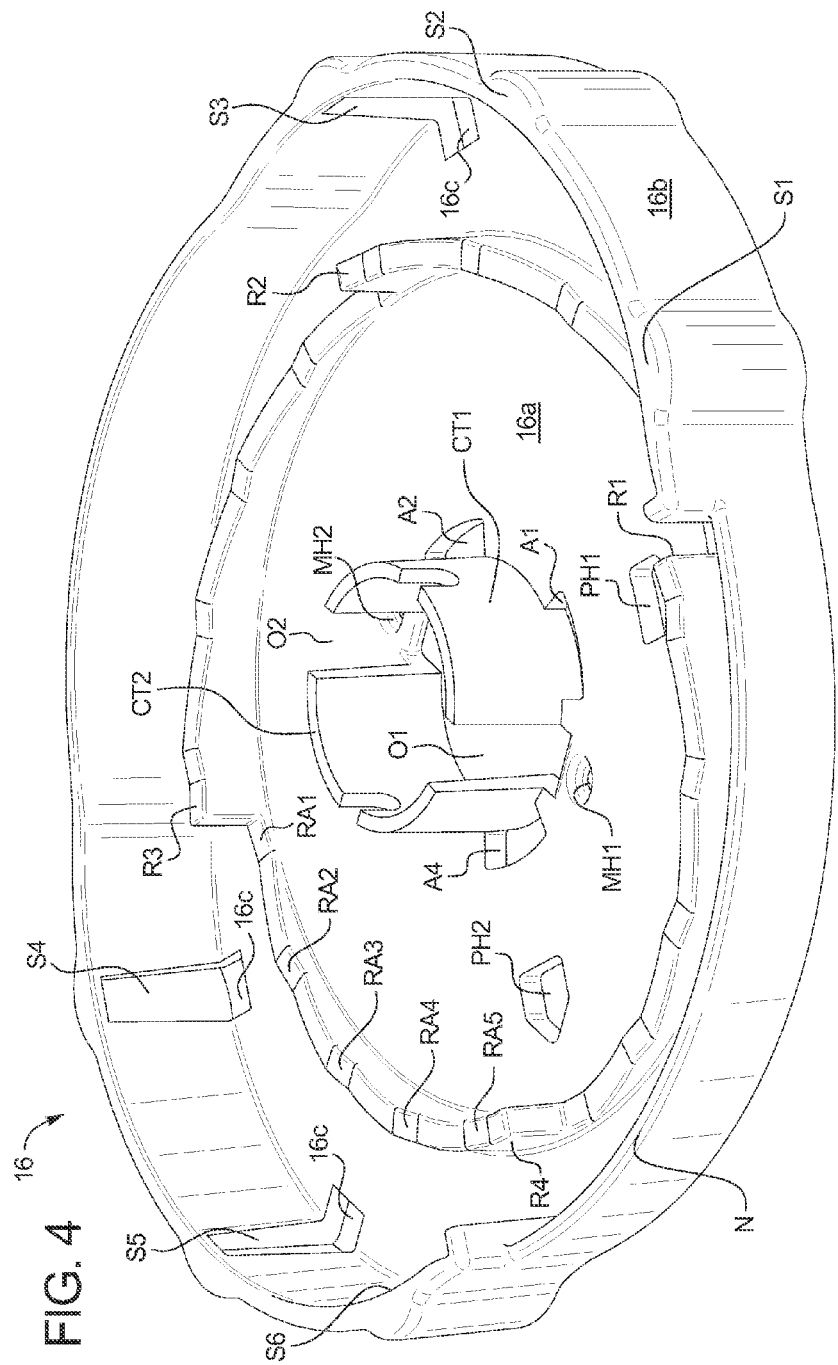
FIG. 4 is a perspective view of one embodiment a top plate of the adjustable pad of the present disclosure.

Base plate 12 of FIG. 2 is also illustrated as having six spring-like, cantilevered fingers F1 to F6 along its outer wall 12c that are bent slightly as the fingers slide along respectively slots S1 to S6 formed on an inner surface of sidewall 16b in top plate 16 of FIG. 4. The tops of fingers F1 to F6 each include outwardly projecting lips 12d that mate with and are pushed by the walls of slots S1 to S2. Apertures 16c are provided in solid outer surface 16a of top plate 16 located at the end of each slot S1 to S6, so that fingers F1 to F6 can travel into slots S1 to S6 if need be to prevent fingers F1 to F6 from bottoming out against outer surface 16a. The felt cushion attached to sheet 18 shown in FIG. 1 again covers the projecting lips 12d, so that the lips do not impact the user. The fitting of fingers lips F1 to F6 into respective slots/apertures S1 to S6 16c also provides (i) rotational stability of base plate 12 relative to top plate 16 and (ii) additional tilting stability of the base plate relative to the top plate.

Figure 5A:
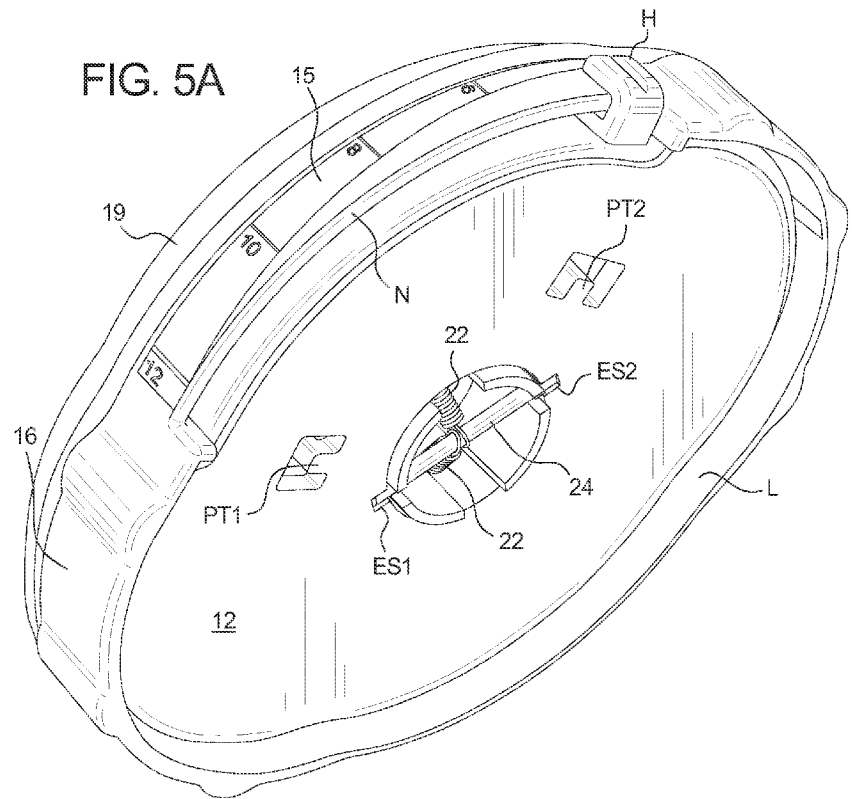
FIG. 5A is a perspective view of one embodiment of an assembled and fully compressed adjustable pad of the present disclosure shown from the base plate side of the pad.

The innermost rings 12a and CT1/CT2 of base plate 12 and top plate 16, respectively, each include matching openings O1 and O2 that allow for the small extension springs 22 shown in FIGS. 1, 5A, 5B and 6 to mount, each on one spring 22 end to a mounting hole MH1 or MH2 of the solid outer surface 16a of top plate 16 and to extend to connect each on their opposing spring 22 end to a rod 24 carried by base plate 12, which is also shown in FIGS. 1, 5A and 5B. Springs 22 can be metal or plastic and in an embodiment include a hook at both ends to releasably latch onto mounting holes MH1 and MH2 or rod 24. Rod 24 can also be metal or plastic and releasably sits in tubular end supports ES1 and ES2 (FIGS. 2 and 5A) located in the solid wall of base plate 12. Rod 24 extends across the central opening in the solid wall of base plate 12 from end support ES1 to end support ES2. The exposed portion of rod 24 accepts the opposing ends of extension springs 22. Extension springs 22 pull base plate 12 and top plate together against adjuster ring 14 of FIG. 3 regardless of the translational position of base plate 12 relative to top plate 16.

Base plate 12 does not rotate relative to top plate 16. The plates instead translate away from or towards each other, such that adjustable pad 10 either expands or contracts. Adjuster ring 14 of FIG. 3 on the other hand rotates relative to both base plate 12 and top plate 16. As shown in the views of FIGS. 2 to 4, adjuster ring 14 sits as it is shown in FIG. 3 with its handle H forming an upwards "U" shape when adjuster ring 14 is placed in base plate 12 and base plate 12 is oriented as it is shown in FIG. 2. Top plate 16 is then turned upside down relative to its position of FIG. 4 (so that S1 and S6 match F1 and F6) to fit over the adjuster ring 14 sitting in base plate 12.

Adjuster ring 14 as illustrated in FIG. 3 includes an inner ring IR, an outer ring OR and spokes SP1 to SP4 extending between the rings. Spokes SP1 to SP4 each have slight positively or outwardly pointing ramp angles on both top and bottom sides of each spoke. That is, the spokes form slightly angled rooftop type shapes on both the upper and lower sides of adjuster ring 14 shown in FIG. 3. The slight positively or outwardly pointing ramp angles of spokes SP1 to SP4 mate with any one of five mating negatively or inwardly pointing ramp angles RA1 to RA5 of a respective inclined ramps R1 to R4. That is, ramp angles RA1 to RA5 are indented, forming a flatly angled V-shape. Ramps R1 to R4 are provided on both base plate 12 and top plate 16. Each of ramps R1 to R4 has the five ramp angles RA1 to RA5. Each ramp angle RA1 to RA5 (i) extends along an incline of the ramp so as to have a different distance from a foot of the ramp than does an adjacent ramp angle and (ii) corresponds to one of the five telescoping expansion/compression settings of adjustable pad 10.

Each of the five expansion/compression settings of adjustable pad 10 is provided on label 15 (shown in FIGS. 1, 5A, 5B and 7) attached to top plate 16. The numbers on the illustrated label correspond to millimeters of adjustment. The lowest number is 4 millimeters ("mm"), which represents the initial starting height of pad 10. There are five positions in the illustrated embodiment, which as illustrated are: 4 mm, 6 mm, 8 mm, 10 mm, and 12 mm. These numbers correspond roughly to 3°, 4.5°, 6°, 7.5°, and 9° of knee compartment correction, respectively. The settings could vary as desired and more or less than five settings could be provided alternatively.

The most compressed position of base plate 12 relative to top plate 16 occurs when adjuster ring 14 is rotated such that all four of its spokes S1 to S4 sit between ramp angles RA1 of each of mating base plate 12 side and top plate 16 side ramps R1/R1, R2/R2, R3/R3 and R4/R4. The second most compressed position of base plate 12 relative to top plate 16 occurs when adjuster ring 14 is rotated such that all four of its spokes SP1 to SP4 sit between ramp angles RA2 of each of mating ramps R1/R1, R2/R2, R3/R3 and R4/R4, and so on. Thus, the most expanded position of base plate 12 relative to top plate 16 occurs when adjuster ring 14 is rotated such that all four of its spokes S1 to S4 sit between ramp angles RA5 of each of mating ramps R1/R1, R2/R2, R3/R3 and R4/R4.

The two springs 22 discussed above hold ramps R1 to R4 sandwiched against spokes SP1 to SP4 of adjuster ring 14. The relatively small springs 22, the relatively slight angles of spokes SP1 to SP4, and the relatively sight angles of mating the ramp angles RA1 to RA5 are not required to hold adjuster ring 14 releasably locked to any of the expansion/compression settings. Additionally, as described above, polygonal spring tabs PT1 and PT2 are provided to lock releasably each into one of the five grooves G provided on the inside of the inner ring IR of adjuster ring 14. Thus each of the five grooves G also corresponds to one of the five expansion/compression settings of adjustable pad 10 device provided on the label. The relatively steep, e.g., 45°, ramp angles of the positively or outwardly angled polygonal spring tabs PT1 and PT2 and mating inwardly angled grooves G provide a good locking force but on the other hand do not require undue force to index adjuster ring 14.

FIG. 5A shows the assembled adjustable pad 10 in its most compressed position from the base plate 12 side of pad 10. Pile layer 20 has been removed to show additional detail on plate 12. Top plate 16 extends past the mated base plate such that a lip L forms around the periphery of this brace hinge mating side of adjustable pad 10. The lip L fits around the periphery of hinge 32 of the knee brace 30 as shown below in FIG. 7. Lip L provides mounting stability to the removeable attachment of pad 10 to hinge 32. For example, lip L makes the twisting of pad 10 relative to hinge 32 difficult, helping to prevent pad 10 from twisting off of hinge 32 and brace 30 by accident. Again, hinge 32 is provided with a hook material that attaches releasably to the pile material provided on base pile layer 20 (FIGS. 1 and 7) adhered to the face of base plate 12. A foam cushion 19 is removably attached to hook sheet 18 (FIGS. 1 and 5B) on the opposing side of pad 10. Foam cushion 19 provides a softened interface with the patient's knee.

As illustrated in FIGS. 4, 5A and 5B, notch N provided in sidewall 16$b$ of top plate 16 allows handle H to travel back and forth to different height adjustment settings for adjustable pad 10. Notch N also provides end of travel stops at the lowest height setting and the largest height setting so that adjuster 14 cannot be moved or rotated any further, which would potentially cause spokes SP1 to SP4 to slip onto a different ramp, e.g., from a largest height setting of the correct ramp immediately to the lowest height setting of an adjacent ramp.

FIG. 5B shows the assembled adjustable pad 10 from the top plate 16 side of the pad. Hook sheet 18 is shown having a hook material hatch. FIG. 5B illustrates certain features of top plate 16 that are more difficult to see in FIGS. 1 and 4, which also illustrate top plate 16. FIG. 5B shows setting label 15 of base plate 12 and handle H of adjuster ring 14. Also illustrated from base plate 12 are spring tip lips 12$d$ of spring-like cantilevered fingers F1 to F6. Lips 12$d$ are illustrated as just meeting or slightly inserted through mating aperture 16$c$ of slots S1 to S6 formed along the inside of sidewall 16$b$ of top plate 16. If it is desired to remove top plate 16 from base plate 12, springs 22 are unhooked from rod 24.

As discussed above, outer surface 16$a$ of top plate 16 (as shown in FIG. 1—needs to be labeled in FIG. 5B) of FIG. 5B defines semi-cylindrical apertures A1 to A4, which respectively accept longitudinally extending tabs LT1 to LT4 as the tabs are translated outwardly or inwardly via the ramp angle settings RA1 to RA5. Likewise, polygonal holes PH1 and PH2 formed in outer surface 16$a$ of top plate 16 receive polygonal tabs PT1 and PT2, respectively, as the tabs are translated outwardly and inwardly via ramp angle settings RA1 to RA5. The engagement of base plate 12 and top plate 16 via each of (i) spring fingers F1 to F6, (ii) longitudinally extending tabs LT1 to LT4 and (iii) polygonal tabs PT1 and PT2 constrains base plate 12 and top plate 16 from rotating or tilting relative to each other as the plates are translated together and apart via ramp angle settings RA1 to RA5. The four spokes and sets of ramp angles also provide an evenly distributed force around the circumference of pad 10.

FIG. 5B also illustrates spring mounting holes MH1 and MH2 defined by outer surface 16A of top plate 16. Spring mount holes MH1 and MH2 each accept one end of two extension springs 22. The other ends of springs 22 hook or otherwise attach to metal or plastic rod 24 positioned in base plate 12. As discussed above, springs 22 compresses base and top plates 12 and 16 to adjuster ring 14 throughout the movement of spokes SP1 to SP4 through ramps R1 to R4 of both base and top plates 12 and 16.

While adjustable pad 10 has been illustrated with angled ramps R1 to R4 on both base and top plates 12 and 16, it is contemplated in an alternative embodiment to provide ramps R1 to R4 having ramp angles, such as ramp angles RA1 to RA5, on only one of base plate 12 and top plate 16. The other plate could have non-changing, constant height semi-cylindrical ridges instead of angled semi-cylindrical ramps R1 to R4, or have no ridges at all. Further, for any embodiment of pad 10, more or less than four ramps may be provided.

Figure 6:
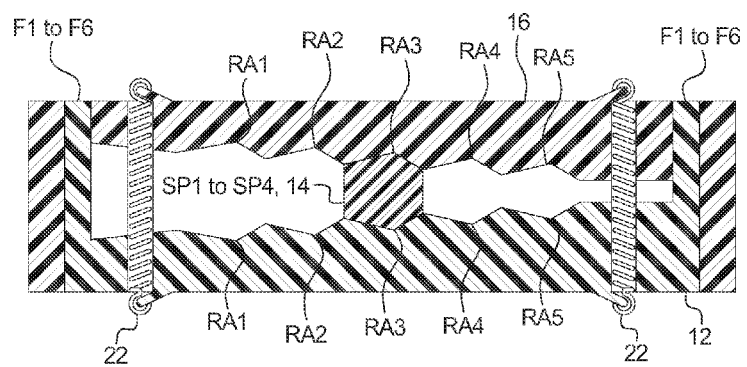
FIG. 6 is a simplified sectioned, schematic view of the one embodiment of an assembled adjustable pad of the present disclosure. (note: the twp ramps actually scissor past one another when the base plate and top plate are fully collapsed—that is why they are adjacent and concentric curved ramps)
Figure 7:
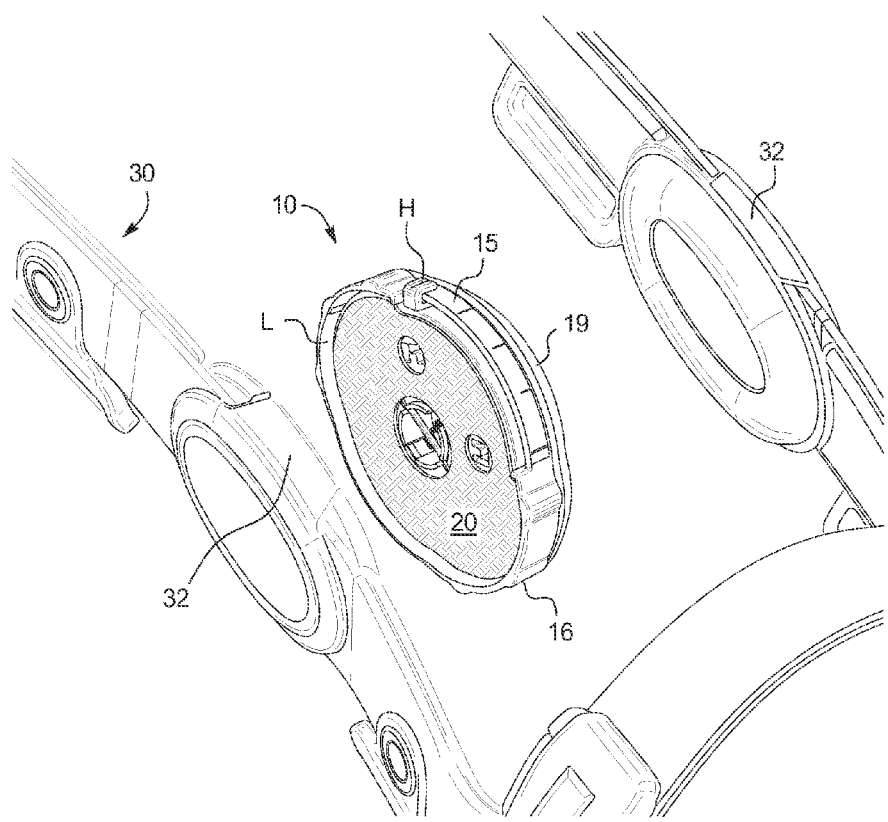
FIG. 7 is a perspective view of one embodiment the adjustable pad of the present disclosure positioned in mounting relationship with an orthopedic knee brace.

Referring now to FIG. 6, a simplified sectioned view of adjustable pad 10 is illustrated. FIG. 6 is not meant to replicate the structures of FIGS. 1 to 5. Instead, FIG. 6 is intended to illustrate the movement and the holding together of pad 10 in a more simplified manner. FIG. 6 also shows base plate 12, adjuster ring 14 and top plate 16 fastened together in a sectioned view, which is helpful (note that in reality the two ramps actually slide past one another when they are completely telescoped closed).

Base plate 12 illustrates ramp angles RA1 to RA5, which can be of any of the orthogonally spaced apart ramps R1 to R4 of the base plate. Likewise, top plate 16 illustrates mating ramp angles RA1 to RA5, which can again be of any of the orthogonally spaced apart ramps R1 to R4 of the top plate. Base plate 12 is also illustrated with fingers F1 to F6 as described above. Base plate 12 and top plate 16 are both illustrated accepting springs 22. While the actual configuration and placement of springs 22 may be different than is shown in FIG. 6, the function and purpose of the springs is conveyed.

The upper and lower positive or outwardly projection rooftop ramp angles or spokes SP1 to SP4 on the upper and lower surface of spokes SP1 to SP4 engage the negative or V-shaped indentations RA1 to RA5 of ramps R1 to R4. As spoke SP1 to SP4 is pushed left to right in FIG. 6, springs 22 and spring, fingers F1 to F6, and polygonal tabs PT1 and PT2 cause the user to feel a resistance as the spoke moves to the next position. Eventually, at the next position, plates 12 and 16 snap together as the greatest height of the cross-section of the spoke moves past the most pinched together opening of the adjacent mated ramp angles. Springs 22 keep compression on the assembly of plates 12 and 16 and adjuster ring 14.

In FIG. 6, spoke SP1 to SP4 is shown positioned at the middle adjustment location between ramp angles RA3 of plates 12 and 16. The collective height of any given adjustment location is the sum of the height of spoke SP1 to SP4 plus the distances of the mated ramp angles to their respective top and bottom of the top and base plates 16 and 12. Thus if spoke SP1 to SP4 is moved to the right between ramp angle RA4, the overall telescoping height of the adjuster 10 increases because the distances between ramp angles RA4 to top and bottom of respective plates 16 and 12 increases relative to that of mated ramp angles RA3. Conversely, if spoke SP1 to SP4 is moved one position to the left, to mated ramp angles RA2, the overall telescoping height of adjuster 10 decreases because the distances between ramp angles RA2 to the top and bottom of respective plates 16 and 12 decreases relative to that of mated ramp angles RA3. Springs 22 compress accordingly to maintain pressure on the ramp and spoke assembly.

It should be appreciated therefore that mated ramp angles RA1 yield the least telescoped overall height, while mated ramp angles RA5 yield the greatest telescoped overall height of adjuster 10. Springs 22 maintain compression on the assembled adjuster pad 10 regardless of the mated ramp angle location RA1 to RA5 to which spoke SP1 to SP4 has been rotated.

As shown in FIG. 7, adjustable pad 10 is placed removably by the user on the inside of one hinge 32 of the brace 30. Pad 10 pushes up against one side or the other side of user's knee. A felt cushion 19 is provided on the inside of pad 10 to make comfortable contact with the user's knee. Most of the time, adjustable pad 10 is positioned at the lateral or outer side of the user's knee because the majority of knee problems are medial (inner) condyle compartment or medial osteoarthritis, requiring adjustable pad 10 to push the knee inward. A small percentage of patients have problems with the lateral (outer) condyle compartment. Here, adjustable pad 10 is switched to the other side of the knee brace and is worn such that adjustable pad 10 is located on the inside of the patient's knee to push outwardly on the patient's knee, thus opening the lateral compartment.

Second Primary Embodiment

Figure 8:
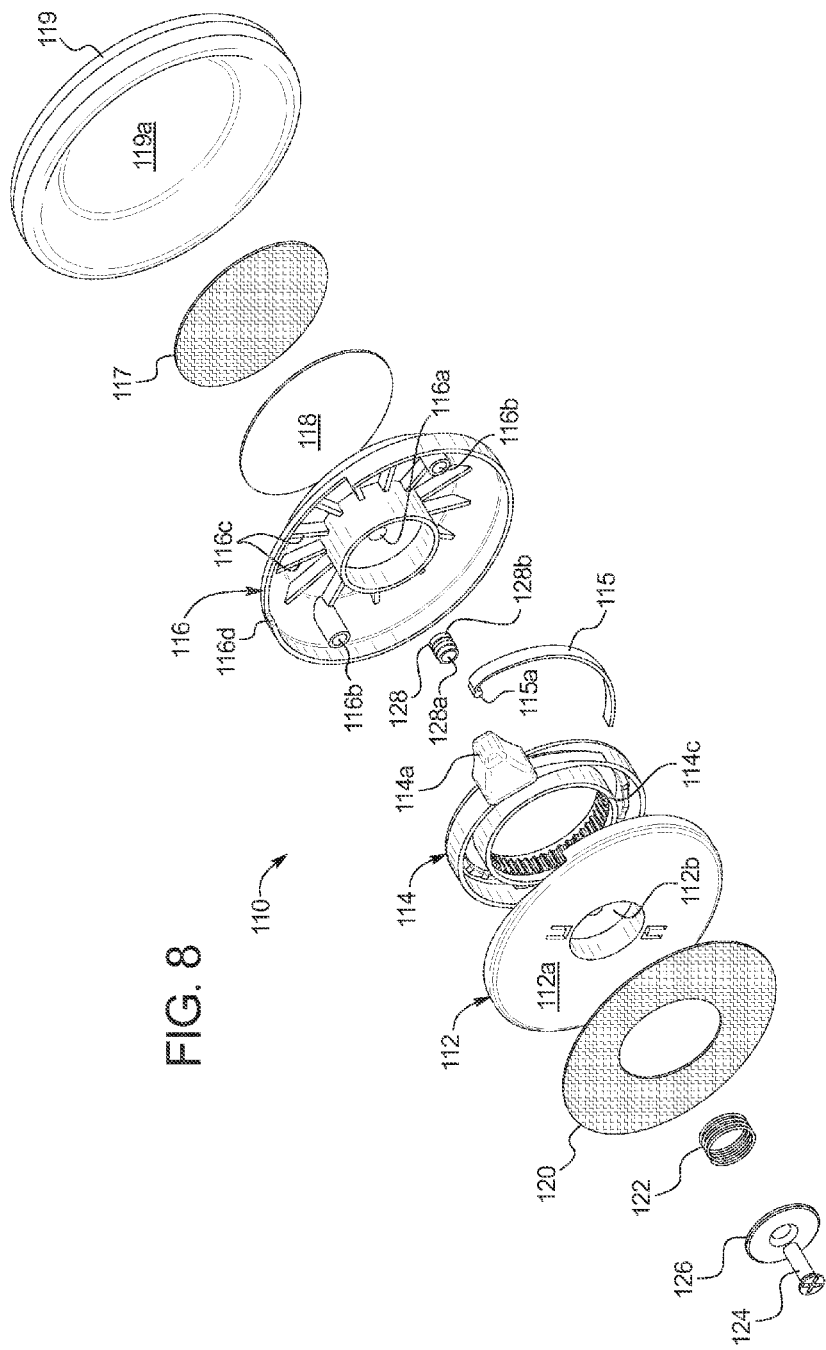
FIG. 8 is an exploded perspective view of an alternative primary embodiment of an adjustable pad of the present disclosure including, from left to right, a mounting screw, a pressure washer, a compression spring, a base hook or pile layer, a base plate, an adjuster, a threaded mounting insert, a top plate, a top plate pile or hook layer, a pad hook or pile layer, and a cushioned pad.

A second primary embodiment for an adjustable pad is shown and described in connection with adjustable pad 110 and FIGS. 8 to 11 as follows. FIG. 8 is an exploded view showing the different pieces of adjustable pad 110. FIG. 8 in general flows oppositely from the flow of FIG. 1. That is, from left to right, adjustable pad 10 in FIG. 1 flows from the side of the pad that abuts the wearer's knee to the side of the pad that attaches to the knee brace. In FIG. 8, adjustable pad 110 flows left to right instead from the side of the pad that attaches to the knee brace to the side of the pad that abuts the wearer's knee.

From left to right, adjustable pad 110 includes a mounting screw or fastener 124, a pressure-applying washer 126, a compression spring 122, a base hook or pile layer 120, a base plate 112, an adjuster ring 114, a label 115, a threaded mounting insert 128, a top plate 116, a top plate pile or hook sheet 118, a pad hook or pile layer 117, and a cushioned pad 119. As mentioned above, for any embodiment of the adjustable pads of the present disclosure, any surface can have hook or pile material interchangeably.

Mounting screw or fastener 124 can be a metal, e.g., steel or stainless steel, screw, such as a flathead screw. Pressure-applying washer 126 can likewise be metal, e.g., steel or stainless steel, and in an embodiment is formed with a chamfered hole that allows the flathead of screw 124 to sit flush with the outer surface of pressure-applying washer 126. Threaded mounting insert 128 can likewise be made of metal, e.g., steel or stainless steel, or be made of a hard plastic.

Base hook or pile layer 120 is applied to, e.g., adhered to, outer surface 112a of base plate 112. Top plate pile or hook sheet 118 is applied to, e.g., adhered to, the outer surface of top plate 116. Pad hook or pile layer 117 is applied to, e.g., adhered to, an inner surface 119a of cushioned pad 119. Adjustable pad 110 is removably attached to hinge 32 of brace 30 via a hook and pile attachment with hook or pile layer 120. Cushioned pad 119 is removably attached to top plate 116 for cushioned contact with the side of a user's knee via a hook and pile attachment between top plate pile or hook sheet 118 and pad hook or pile layer 117. Label 115 can be attached to, e.g., adhered to, any of base plate 112, adjuster ring 114 (discussed in more detail below) or top plate 116. Label 115 can include the same or different, more or less, demarcations as label 15 discussed above. Base plate 112, adjuster 114 and top plate 116 can be metal or plastic, e.g., molded plastic, and be made of any of the materials discussed above for base plate 12, adjuster 14 and top plate 16.

Threaded mounting insert 128 is molded into or press-fit into a central aperture 116a formed in top plate 116. Base end 128a of threaded mounting insert 128 is female threaded to threadingly receive screw 124. Top end 128b of threaded mounting insert 128 can be blind or solid to provide a hard stop for screw 124. Or, aperture 116a can be a blind aperture and provide a hard stop for screw 124, allowing insert 128 to be open on both ends 128a and 128b. Screw 124 can be glued into place within threaded mounting insert 128. Alternatively, threaded mounting insert 128 can be lined with a self-locking liner, such as a nylon liner used with self-locking nuts or aircraft type nuts. Insert 128 can have a portion that extends out from aperture 116a or be fully inserted into aperture 116a, such that base end 128a is at least substantially flush with aperture 116a.

With threaded mounting insert 128 fixed to top plate 116, screw 124 extends through pressure-applying washer 126, spring 122, base plate 112 and adjuster ring 114 and fastens to threaded base end 128a of threaded mounting insert 128, capturing pressure-applying washer 126, spring 122, base plate 112, adjuster ring 114 and top plate 116 together forming an assembled adjustable pad 110. Screw 124 in this manner holds adjustable pad 110 together.

Spring 122 is compressed between washer 126 and an offset surface 112b of base plate 112. In this configuration, compression spring 122 presses base plate 112, adjuster ring 114, and top plate 116 together for operation. When spring 122 is fully compressed, assembled adjustable pad 110 cannot be further expanded. The most expanded setting along label 15 is therefore configured to occur before spring 122 is fully compressed.

When adjustable pad 110 is in its most compressed state, spring 122 is in its most expanded state but is still compressed enough to apply a suitable holding force to hold base plate 112, adjuster ring 114, and top plate 116 together for operation. Here, the head of screw 124 may extend out past outer surface 112a and hook or pile layer 120. Hinge 32 of brace 30 can have a natural recess or open area for accepting the extended head of screw 124, so that the screw does not interfere with the hook and pile attachment between adjustable pad 110 and hinge 32. Alternatively, the amount that surface 112b is offset from outer surface 112a of base plate 112 and/or the length of screw 124 are selected so that the head of screw 124 does not extend outwardly past outer surface 112a and hook or pile layer 120 regardless of how compressed adjustable pad 110 becomes.

Top plate 116 includes receiver posts 116b that extend towards base plate 112. Receiver posts 116b receive mating studs 112c (FIG. 10) extending from an inside of base plate 112 towards top plate 116. The mating of receiver posts 116b and studs 112c provides adjustable pad 110 with the rotational and tilt stability as has been discussed above for adjustable pad 10. More than two receiver posts 116b and mating studs 112c can be provided alternatively to help prevent the tilting and rotating of top plate 116 relative to base plate 112. Receiver posts 116b can lead to openings in the top wall of top plate 116 or studs 112c can be short enough such that the studs do not bottom out against the inside of the top wall of top plate 116 even when adjustable pad 110 is fully compressed. As with pad 10, cushioned pad 119 will negate any user detection or feeling of studs 112c if the studs extend out past the top wall of top plate 116.

Adjuster ring 114 includes a handle 114a that enables the user to grasp and turn adjuster ring 114. While adjusters 14 and 114 have been described as rings, it should be appreciated that the adjusters could alternatively be linearly actuated adjusters and therefore do not have to be adjuster rings.

Figure 9:
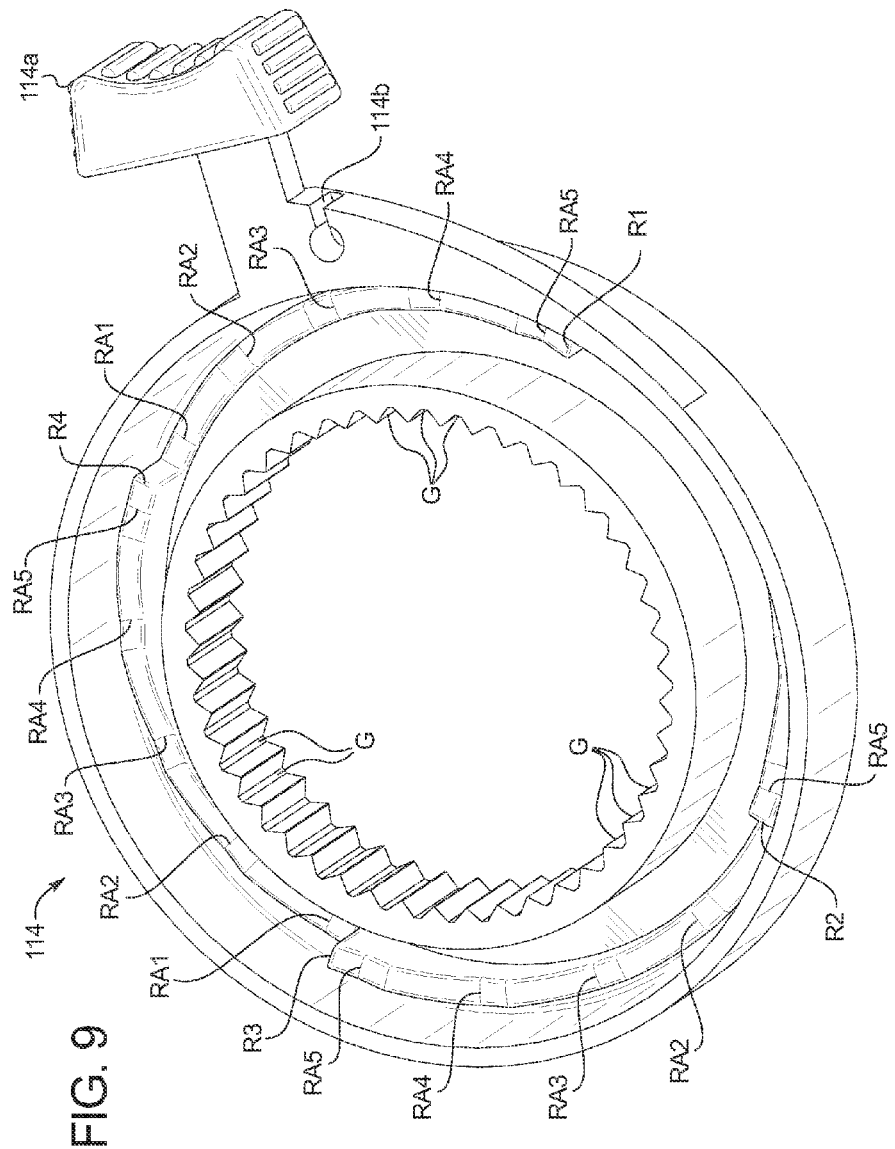
FIG. 9 is a perspective view of one embodiment of the adjuster of the primary embodiment of FIG. 8.

Referring now to FIG. 9, adjuster 114 is illustrated in more detail. With pad 10, ramps R1 to R4 are provided on one or both of base plate 12 and top plate 16, while spokes SP1 to SP4 are provided on adjuster 14. With pad 110 on the other hand, a plurality of ramps are provided instead on one or both sides of adjuster 114. Adjuster 114 includes four ramps R1 to R4 as before, each ramp including five ramp angles RA1 to RA5. Adjuster 114 can alternatively include more or less ramps having more or less ramp angles. While ramps R1 to R4 can be provided on one or both sides of adjuster 114, in the illustrated embodiment, ramps R1 to R4 are provided only on the side of adjuster 114 that faces base plate 112.

Adjuster 114 also includes or defines a notch 114b that receives a head portion 115a of label 115. Notch 114b helps to hold and orient label for connection to adjuster 114. With adjustable pad 10, the handle H moved relative to stationary label 15. In the illustrated embodiment of adjustable pad 110, label 115 moves along with handle 114a. Base plate 112 and/or top plate 116 therefore need only provide a mark that aligns with one of the moveable indicia of label 115 to indicate a current height setting.

FIG. 9 also illustrates that adjuster 114 includes an inner tubular collar 114c including or providing a plurality of inwardly disposed V-shaped grooves G. In the illustrated embodiment, V-shaped grooves G span the entire three-hundred sixty degree inner circumference of inner tubular collar 114c.

Figure 10:
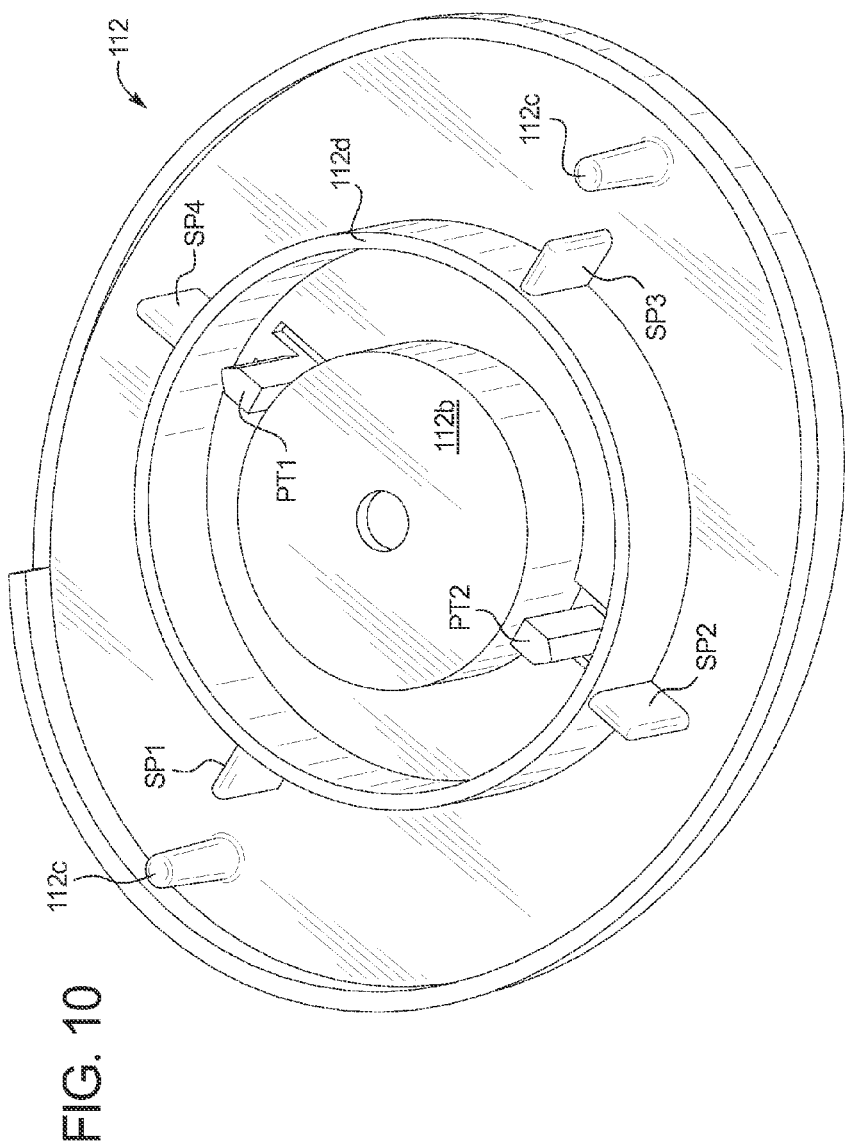
FIG. 10 is a perspective view of one embodiment of the base plate of the primary embodiment of FIG. 8.

Referring now to FIG. 10, the side of base plate 112 that mates with ramps R1 to R4 of adjuster 114 is illustrated. Offset surface 112b of base plate 112 described above for receiving and interacting with spring 122 is illustrated. Offset surface 112b also defines a central hole for receiving screw 124. Alignment studs 112c discussed above for insertion into receiver posts 116b of top plate 116 for tilt and rotational stability are also illustrated.

Base plate 112 includes a spoke ring 112d that provides structural rigidity to base plate 112 itself as well as to spokes SP1 to SP4 connected at their inner ends to spoke ring 112d. Spokes SP1 to SP4 are paddle shaped as opposed to the ramped or double-ramped polygonal shapes of spokes SP1 to SP4 of adjustable pad 10. Paddle shaped spokes SP1 to SP4 are slender and rounded along their surfaces for interacting with ramp angles RA1 to RA5 and are thus readily able to snap fit into the female V-shaped grooves of the ramp angles. As before, each ramp angle RA1 to RA5 extends along an incline of the ramp so as to have a different distance from a foot of the ramp than does an adjacent ramp angle. In the illustrate embodiment, like above with adjustable pad 10, spoke SP1 of base plate 112 is dedicated to ramp R1 of adjuster 114, spoke SP2 of base plate 112 is dedicated to ramp R2 of adjuster 114, spoke SP3 of base plate 112 is dedicated to ramp R3 of adjuster 114, and spoke SP4 of base plate 112 is dedicated to ramp R4 of adjuster 114.

Spokes SP1 to SP4 ride along the changing height of ramp angles RA1 to RA5 of ramps R1 to R5, respectively, changing the overall height in the manner illustrated in connection with FIG. 6. Here, as opposed to FIG. 6, only one set of ramps R1 to R4 is provided. Nevertheless, the mode of changing the height of adjustable pad 110 is aptly illustrated by FIG. 6. And as has been described, spring 122 holds spokes SP1 to SP4 to ramps R1 to R4, respectively, regardless of which ramp angle RA1 to RA5 is selected and applied.

Referring additionally to FIG. 8, top piece 116 provides radially extending paddles 116c. Paddles 116c could be modified to be spokes that operate with a second set of ramps extending from adjuster 114 towards top plate 116. In the illustrated embodiment, however, radially extending paddles 116c serve to provide rigidity to top plate 116 and to space or center adjuster 114 within top plate 116 for proper operation. Top plate also includes or defines a notch 116d that limits the travel of handle 114a and adjuster 114 about base plate 112 and top plate 116, maintaining lining a set relationship between spokes SP1 to SP4 and respective ramps R1 to R4 as has been described with notch N of adjustable pad 10.

FIG. 10 also shows that top piece 116 includes or defines polygonal tabs PT1 and PT2 that serve largely the same purpose as the polygonal tabs PT1 and PT2 of adjustable pad 10. Polygonal tabs PT1 and PT2 of top plate 116 are spring-like and include outwardly facing triangular shapes that bendingly snap-fit into mating contact with multiple ones of V-shaped grooves G spanning the circumference of inner tubular collar 114c of adjuster 114. The snap-fitting connection between polygonal tabs PT1 and PT2 and grooves G provides tactile feedback to the user. The snap-fitting connection also holds adjustable pad 110 in a desired telescoped height setting.

The many V-shaped grooves G can provide a finer amount of adjustability than do the five ramp angle setting shown above. That is, a ramp angle could be provided for each groove G per ramp R1 to R4. Thus if there are twelve grooves G per ramp R1 to R4, there could be twelve ramp angles RA1 to RA12. The four mm to twelve mm pad height adjustment discussed above could be divided into twelve setting instead of the five shown above. Or, the height adjustment range could be expanded over the twelve settings, e.g., four mm to 12.25 mm over 0.75 mm increments, or four mm to fifteen mm over 1.00 mm increments. There can also be more or less than twelve grooves G per ramp. In any case, the grooves G and polygonal tables PT1 to . . . PTn hold adjuster 114 and adjustable pad 110 in a set position until modified by the user.

Figure 11:
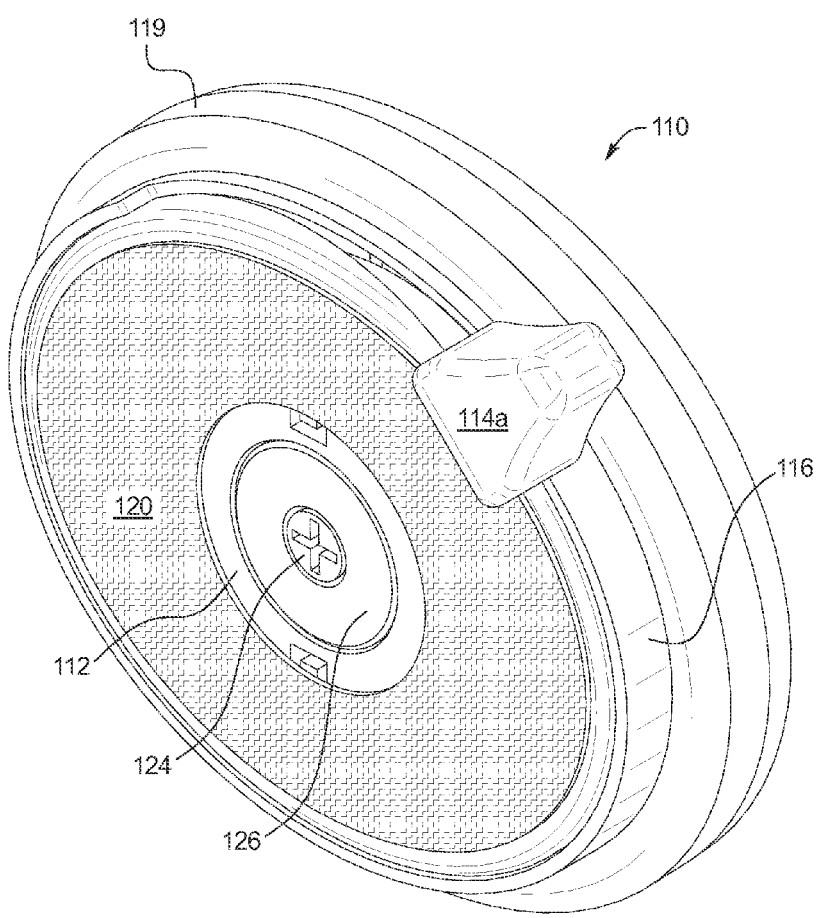
FIG. 11 is a perspective view of one embodiment of an assembled adjustable pad of the primary embodiment of FIG. 8.

Referring now to FIG. 11, an assembled adjustable pad 110 is illustrated. Base hook or pile layer 120 is exposed so that pad 110 can be removably attached to hinge 32 of brace 30. Screw 124 is shown being flush with press-applying washer 126, both of which are in turn substantially flush with base plate 112. Base plate 112 could be pushed inwardly from screw 124 and washer 126, in which case screw 124 and washer 126 can reside inside a recess of hinge 32, allowing base hook or pile layer 120 to be fastened to the mating pile or hook material of brace hinge 32. Gel cushioned and/or foam padding cushioned pad 119 is removably fastened to adjustable pad 110 for cushioned impact with the side of the user's knee. Handle 114c is available to be rotatably pushed or pulled to change a height adjustment setting.

Associated Methodology

As mentioned in the SUMMARY, the apparatuses of the present disclosure operate via methods to provide a varied amount of side load on a user's knee. The method includes enabling a user to turn or maneuver a handle provided by a removable telescoping pad that can be placed on the medial or lateral side of a user's knee. The handle moves or turns a structure, such as an adjustable ring. The ring can have a spoke for example. The turning of the causes the ring, e.g., spoke, to wedge into a new set of features, e.g., ramp angles, provided by first and second plates surrounding the adjustable ring. The wedging of the ring into the new set of features causes a telescoping expansion or compression of the assembly to apply a changed side load to the knee. A spring compression force is supplied to compress the plates to the adjustable ring during adjustment or changing of the wedge.

In the above method, the ramp angles and associate ramps are provided on one or both sides of the adjuster ring, either physically on the plates or on the adjuster itself, while the spokes or other ramp angle mating features are provided alternatively on the adjuster or on one or both of the mating first and second plates. As shown above, the spring can be an extension spring that is pulled apart and is biased to compress back to its natural shape to provide the compressive force. The spring can alternatively be a compression spring that is pushed together and is biased to expand back its natural shape to provide the compressive force.

It should be understood that various changes and modifications to the presently preferred embodiments described herein will be apparent to those skilled in the art. For example, many features of the top plate could be provided instead on the base plate and vice versa. This is reflected below in the claims. Such changes and modifications can be made without departing from the spirit and scope of the present subject matter and without diminishing its intended advantages. It is therefore intended that such changes and modifications be covered by the appended claims.

The invention is claimed as follows:

1. An orthopedic apparatus comprising:
an orthopedic knee brace; and
a telescoping adjustable pad removably attachable to the orthopedic knee brace, the telescoping adjustable pad including
a top plate,
a base plate,
an adjuster located between the top plate and the base plate,
at least one ramp including a plurality of ramp angles, the at least one ramp inclined so that at least two of the plurality of ramp angles are spaced differently from a foot of the at least one ramp,
at least one spoke positioned and arranged to selectively engage one of the plurality of ramp angles of the at least one ramp, and wherein
(i) the at least one ramp is provided on one side of the adjuster and the at least one spoke is provided on one of the top plate or the base plate, (ii) the at least one ramp is provided on each of two sides of the adjuster and the at least one spoke is provided on each of the top plate and the base plate, (iii) the at least one ramp is provided on one of the top plate or the base plate and the at least one spoke is provided on a mating side of the adjuster, or (iv) the at least one ramp is provided on each of the top plate and the base plate and the at least one spoke is provided on each of two sides of the adjuster.

2. The orthopedic apparatus of claim 1, wherein one of the top or the base plates includes at least one tab that extends in a cantilevered manner from a wall of the one of the top or the base plates, the adjuster including at least one receiving feature for receiving a mating feature of the at least one tab, the at least one receiving feature and the mating feature coinciding with an adjustment setting of the telescoping adjustable pad.

3. The orthopedic apparatus of claim 2, wherein the adjuster includes an interior ring forming the at least one receiving feature.

4. The orthopedic apparatus of claim 2, wherein the other of the top or base plate defines at least one aperture for receiving the at least one tab to allow the telescoping adjustable pad to be compressed without the at least one tab abutting the other of the top or base plate.

5. The orthopedic apparatus of claim 1, wherein the at least one ramp is compressed against the at least one spoke by at least one spring.

6. The orthopedic apparatus of claim 5, wherein the at least one spring is (i) an extension spring in mechanical communication with the top and base plates, or (ii) a compression spring biased to apply a compression force to the top plate or the base plate.

7. The orthopedic apparatus of claim 1, wherein the telescoping adjustable pad is removably attachable to the orthopedic knee brace via a hook and loop attachment.

8. The orthopedic apparatus of claim 1, wherein the orthopedic knee brace includes medial and lateral hinges, and wherein the telescoping adjustable pad can be selectively attached to either of the medial and lateral hinges.

9. The orthopedic apparatus of claim 1, wherein for (iv) the top plate and the base plate are positioned relative to each other such that the at least one ramp of the top plate is concentric with and adjacent to the at least one ramp of the base plate.

10. The orthopedic apparatus of claim 1, wherein for (iii) the at least one spoke includes a ramp angle that is shaped to mate with ramp angles of the one of the top plate or the base plate, or for (iv) the at least one spoke includes at least one of an upper ramp angle that is shaped to mate with ramp angles of the top plate and a lower ramp angle that is shaped to mate with ramp angles of the base plate.

11. The orthopedic apparatus of claim 1, wherein for (iii) the one of the top plate or the base plate includes N number of ramps, and the adjuster includes N number of spokes for operation with the N number of ramps, or for (iv) at least one of the top plate and the base plate includes N number of ramps, and the adjuster includes at least one of N number of spokes for operation with the N number of ramps of the top plate or N number of spokes for operation with the N number of ramps of the base plate.

12. The orthopedic apparatus of claim 1, wherein the adjuster rotates relative to the top and base plates.

13. The orthopedic apparatus of claim 1, wherein the adjuster includes a handle for a user to rotate the adjuster for setting adjustment, the handle extending from the adjuster so as to reside outside of the top plate and base plate when the base and top plates are mated.

14. The orthopedic apparatus of claim 1, wherein one of the base plate or top plate includes at least one finger extending from a wall of the one of the base plate or the top plate, and the other of the base plate or the top plate includes at least one receiver post or aperture for capturing the at least one finger for stabilizing the base and top plates when the base and top plates are moved towards or away from each other.

15. The orthopedic apparatus of claim 1, wherein one of the top plate or the base plate is configured to be removably attached to the orthopedic knee brace, while the other of the top or the base plate includes or is attached to padding for comfortable engagement with a user of the orthopedic apparatus.

16. The orthopedic apparatus of claim 1, wherein one of the top plate or the base plate includes a lip that extends past the other of the top or base plate, the lip sized and arranged to fit around a periphery of at least one hinge of the orthopedic knee brace to provide mounting stability.

17. The orthopedic apparatus of claim 1, wherein for (i), the at least one spoke is provided on the base plate, and for (i) or (ii), the at least one ramp on the adjuster is configured to engage the at least one spoke provided on the base plate, and wherein for (i) or (ii), a fastener extends through the base plate and is attached to the top plate.

18. The orthopedic apparatus of claim 1, wherein the adjuster is configured to translate the top plate towards and away from the base plate.

* * * * *